US010946346B2

(12) United States Patent
Zhao et al.

(10) Patent No.: US 10,946,346 B2
(45) Date of Patent: Mar. 16, 2021

(54) SPERM SEPARATION BY ELECTROPHORESIS

(71) Applicant: Memphasys Limited, Homebush West (AU)

(72) Inventors: Xing Feng Zhao, North Rocks (AU); Hani Nur, Kellyville (AU)

(73) Assignee: Memphasys Limited, New South Wales (AU)

( * ) Notice: Subject to any disclaimer, the term of this patent is extended or adjusted under 35 U.S.C. 154(b) by 0 days.

(21) Appl. No.: 16/343,680

(22) PCT Filed: Oct. 20, 2017

(86) PCT No.: PCT/AU2017/051137
§ 371 (c)(1),
(2) Date: Apr. 19, 2019

(87) PCT Pub. No.: WO2018/071978
PCT Pub. Date: Apr. 26, 2018

(65) Prior Publication Data
US 2019/0275475 A1     Sep. 12, 2019

(30) Foreign Application Priority Data

Oct. 20, 2016  (AU) ............................... 2016904263

(51) Int. Cl.
| | |
|---|---|
| *B01D 61/42* | (2006.01) |
| *B01D 71/38* | (2006.01) |
| *C12N 5/076* | (2010.01) |
| *B01D 57/02* | (2006.01) |

(52) U.S. Cl.
CPC ............. *B01D 71/38* (2013.01); *B01D 57/02* (2013.01); *B01D 61/42* (2013.01); *C12N 5/061* (2013.01)

(58) Field of Classification Search
CPC ........ B01D 71/38; B01D 57/02; B01D 61/42; C12N 5/061
See application file for complete search history.

(56) References Cited

U.S. PATENT DOCUMENTS

| | | | |
|---|---|---|---|
| 8,123,924 B2 * | 2/2012 | Aitken .................. | B01D 71/50 204/456 |
| 2009/0101507 A1 | 4/2009 | Aitken et al. | |

FOREIGN PATENT DOCUMENTS

| | | |
|---|---|---|
| WO | WO 02/068100 A1 | 9/2002 |
| WO | WO 2013/136091 A1 | 9/2013 |
| WO | WO 2013/186567 A1 | 12/2013 |
| WO | WO 2017/181240 A1 | 10/2017 |

OTHER PUBLICATIONS

International Search Report issued in International Application No. PCT/AU2017/051137, dated Nov. 8, 2017.

* cited by examiner

*Primary Examiner* — Arun S Phasge
(74) *Attorney, Agent, or Firm* — Morse, Barnes-Brown & Pendleton, P.C.; Lisa M. Warren, Esq.; Stanley F. Chalvire, Esq.

(57) ABSTRACT

The present invention relates to the separation of sperm. In particular, the present invention relates to the use of polyvinyl alcohol membranes in the electrophoretic separation of sperm.

13 Claims, 2 Drawing Sheets

SPERM SEPARATION BY ELECTROPHORESIS

This present application is a national stage filing under 35 U.S.C. 371 of International Application No. PCT/AU2017/051137, filed Oct. 20, 2017, which claims priority from Australian Provisional Application No. 2016904263, filed Oct. 20, 2016, the contents of which are incorporated in their entirety herein. International Application No. PCT/AU2017/051137 was published under PCT Article 21(2) in English.

FIELD OF THE INVENTION

The present invention relates to the separation of sperm. In particular, the present invention relates to the use of polyvinyl alcohol membranes for electrophoretic separation of sperm.

BACKGROUND OF THE INVENTION

Any discussion of the prior art throughout the specification should in no way be considered as an admission that such prior art is widely known or forms part of common general knowledge in the field.

One of the major challenges for assisted reproduction technologies (ART) is to devise methods for the preparation of sperm that are fast, efficient and capable of isolating functional sperm without damaging them.

Swim-up techniques and density gradient centrifugation have been widely adopted by the ART industry for separating sperm, but have disadvantages. The swim-up technique is dependent on the motility of the sperm and is not an effective technique for patients with compromised sperm motility. Swim-up techniques may also expose sperm to oxidative stress if the semen sample is contaminated with leukocytes (Aitken & Clarkson, *J. Androl.* 1988, 9: 367-376; Baker et al., *Fertil. Steril.* 1996, 65: 411-419). Centrifugation through discontinuous density gradients overcomes some of the problems associated with the swim-up technique and has been widely accepted as the standard method of sperm separation for ART (Aitken et al., *Biol. Reprod.* 1998, 59: 1037-1046). However, the discontinuous density gradient methods are not effective in samples containing small numbers of motile sperm or samples that are poorly liquefied (Mortimer, *Reprod. Fertil. Dev.* 1994, 6: 25-31). Furthermore, the method can increase levels of oxidative DNA damage in the sperm (Aitken et al., *Hum. Reprod.* 2010, 25: 2415-2426).

Electrophoretic sperm separation represents a viable alternative to swim-up techniques and density gradient centrifugation for the separation of sperm. The method is based on the observation that good quality sperm are characterized by having a negative charge (Ainsworth et al., *Human Reprod.* 2005, 20: 2261-2270).

Electrophoresis is the motion of dispersed particles relative to a fluid under the influence of an electric field. The combination of electrophoresis with a porous membrane, which allows the passage of macromolecules or cells of particular sizes and/or charges, enables the separation and/or purification of macromolecules or cells.

In electrophoretic separation of macromolecules or cells, a porous size exclusion membrane (separation membrane) is used to put into contact two liquids, between which the transfer of macromolecules or cells takes place under the influence of an electric field generated perpendicular to the separation membrane (Galier & Roux-de Balmann, *J. Membrane Sci.* 2004, 241: 79-87; Saxena et al., *Adv. Colloid Interface Sci.* 2009, 145: 1-22). Sample and harvest chambers are formed using two restriction membranes located on either side of a separation membrane (FIG. 1). The restriction membranes have very small pore sizes, which retain aqueous solutions with trans-membrane pressure but conduct current when used with an ionic buffer (Horvath et al., *Electrophoresis* 1994, 15 (1), 968-971).

Electrophoresis has previously been used in the separation of sperm (U.S. Pat. No. 8,123,924; Aitken et al., *Hum Reprod.* 2011, 26(8):1955-1964), with the isolated sperm being relatively free from DNA damage (Ainsworth et al., *Human Reprod.* 2005, 20: 2261-2270) or oxidative stress (Aitken et al., *Hum Reprod.* 2011, 26(8):1955-1964). In brief, viable sperm (which are negatively charged) migrate towards the positive cathode and pass through a separation membrane. Non-viable sperm and other cells do not move, migrate towards the negative electrode, or are unable to pass through the separation membrane (see FIG. 2).

However, existing methods for the electrophoretic separation of sperm involve the use of polyacrylamide (PAm) restriction membranes which compromises the use of the separated sperm in ART. This is due to the possible presence of toxic acrylamide (Am) monomer in the membranes, which may contaminate the separated sperm.

Accordingly, there is a need for alternative membranes suitable for use in the electrophoretic separation of sperm, wherein the membranes are easy and safe to manufacture and wherein the membranes do not contaminate sperm passing through the membrane or coming into contact with the membrane.

It is an object of the present invention to overcome or ameliorate at least one of the disadvantages of the prior art, or to provide a useful alternative.

SUMMARY OF THE INVENTION

The present inventors have found that poly (vinyl alcohol) (PVA) membranes are suitable for use in the electrophoretic separation of sperm.

In one aspect, the present invention relates to use of at least one polymeric membrane in the separation of sperm by electrophoresis, wherein the membrane comprises PVA.

In one aspect, the membrane comprising PVA does not contain PAm.

In another embodiment, the membrane comprising PVA is a membrane that allows passage of an electrical field but does not allow passage of sperm (a restriction membrane).

In another embodiment, the membrane comprising PVA is a porous size exclusion membrane (a separation membrane).

In another embodiment, the PVA has a molecular weight in the range of 6,000 to 186,000 Da, preferably 20,000 to 100,000 Da.

In another embodiment, the concentration of the PVA in the membrane in the range of 5 to 40% w/w, preferably 5 to 15% w/w.

In another embodiment, the membrane further comprises an additional polymer.

In another embodiment, the additional polymer is poly(ethylene glycol) (PEG) or poly(N-vinylpyrrolidone) (PVPON).

In another embodiment, the molecular weight of the additional polymer is in the range of 1,000 to 60,000 da.

In another embodiment, the concentration of the additional polymer in the membrane is in the range of 0.5 to 3% w/w.

In another embodiment, the restriction membrane has a molecular weight cut off (MWCO) of less than 15 kDa.

In another embodiment, the restriction membrane has a MWCO of less than 5 kDa.

In another embodiment, the separation membrane has a pore size of less than 10 µm.

In another embodiment, the separation membrane has a pore size of less than 8 µm.

In another embodiment, the separation membrane has a pore size of less than 5 µm.

In another embodiment, the separation membrane allows passage of viable sperm.

In another embodiment, the separation membrane does not allow passage of non-viable sperm or non-sperm cell types.

In another embodiment, the membrane comprises a support substrate.

In another embodiment, the substrate is a non-woven material and hydrophilic in nature. Suitable materials include, but are not limited to, polyethylene terephthalate (PET), PVA, nylon, cellulose and cellulose derivatives.

In another embodiment, the restriction membrane is prepared by a casting and annealing method.

In another embodiment, the method for preparing the restriction membrane comprises the steps of:
polymer solution preparation;
casting in appropriate casting unit/tank;
drying of the membrane;
annealing at appropriate temperature in an oven; and
cooling and storage.

In another embodiment, the separation membrane is prepared by non-solvent induced phase inversion method followed by post annealing.

In another embodiment, the method for preparing the separation membrane comprises the steps of:
polymer solution preparation;
casting in appropriate casting unit/tank;
non-solvent induced phase inversion;
annealing at appropriate temperature in an oven; and
cooling and storage.

In another embodiment, the non-solvent used in the phase inversion process is an alcoholic system.

In another embodiment, the alcoholic system comprises ethanol and methanol.

In another embodiment, the alcoholic system comprises isopropyl alcohol and acetone.

In another aspect, the present invention relates to a method for separating sperm from a first solution into a second solution, the method comprising the steps of:
providing the first solution to a membrane stack comprising a separation membrane disposed between first and second restriction membranes, wherein the restriction membranes comprise PVA, wherein the first solution lies between the first restriction membrane and the separation membrane and wherein the separation membrane has a preselected pore size; and
applying an electrical field across the stack,
wherein sperm in the first solution that have a negative charge and are smaller than the preselected pore size move towards the anode and pass through the separation membrane into the second solution which lies between the separation membrane and the second restriction membrane.

In another embodiment, the restriction and separation membranes do not contain PAm.

In another embodiment, the separation membrane comprises PVA.

In another embodiment, the separation membrane comprises polycarbonate.

In another embodiment, the separation membrane allows passage of viable sperm.

In another embodiment, the separation membrane does not allow passage of non-viable sperm or non-sperm cell types.

In another aspect, the present invention relates to a method for separating sperm from a first solution into a second solution, the method comprising the steps of:
separating the first and second solutions by means of a separation membrane, wherein the separation membrane comprises PVA and has a preselected pore size;
applying an electric field across the first and second solutions, wherein sperm in the first solution that have a negative charge and are smaller than the preselected pore size move towards the anode and pass through the separation membrane into the second solution.

In another embodiment, the separation membrane does not contain PAm.

In another embodiment, the separation membrane allows passage of viable sperm.

In another embodiment, the separation membrane does not allow passage of non-viable sperm or non-sperm cell types.

In another aspect, the present invention relates to an electrophoresis system for separating sperm, the system comprising:
a separation membrane disposed between two restriction membranes defining first and second fluid chambers, wherein the restriction membranes comprise PVA; and
means for providing an electric field passing from the first fluid chamber to the second fluid chamber through the separation membrane.

In another embodiment, the restriction and separation membranes do not contain PAm.

In another embodiment, the separation membrane comprises PVA.

In another embodiment, the separation membrane comprises polycarbonate.

In another embodiment, the separation membrane allows passage of viable sperm.

In another embodiment, the separation membrane does not allow passage of non-viable sperm or non-sperm cell types.

In the context of the present invention, the words "comprise", "comprising" and the like are to be construed in their inclusive, as opposed to their exclusive, sense, that is in the sense of "including, but not limited to".

As used herein, the term "separation membrane" means a porous size exclusion membrane.

As used herein, the term "restriction membrane" means a membrane that allows the passage of an electrical field but does not allow the passage of sperm.

As used herein the term "PAm" means polyacrylamide.

As used herein the term "PVA" means poly (vinyl alcohol).

As used herein the terms "MWCO" or "molecular weight cut off" in relation to a membrane refers to the to the lowest molecular weight solute (in daltons) wherein at least 90% of the solute is retained by the membrane, or the approximate molecular weight of a molecule that is 90% retained by the membrane.

As used herein the term "pore size" in relation to a membrane refers to the diameter of a macromolecule or cell that is retained by the membrane.

PREFERRED EMBODIMENT OF THE INVENTION

Figure 1:
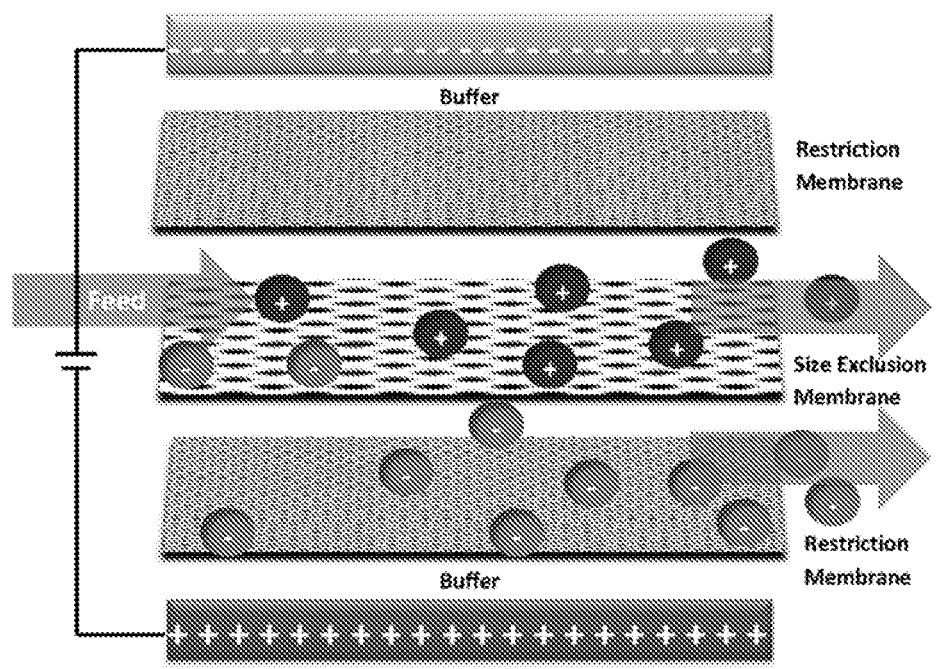
FIG. 1: Operating principle of electrophoretic separation. Fractionation of macromolecules or cells is achieved either through differences in macromolecular charge or electrophoretic mobility; or membrane size exclusion due to differences in macromolecular radius.
Figure 2:
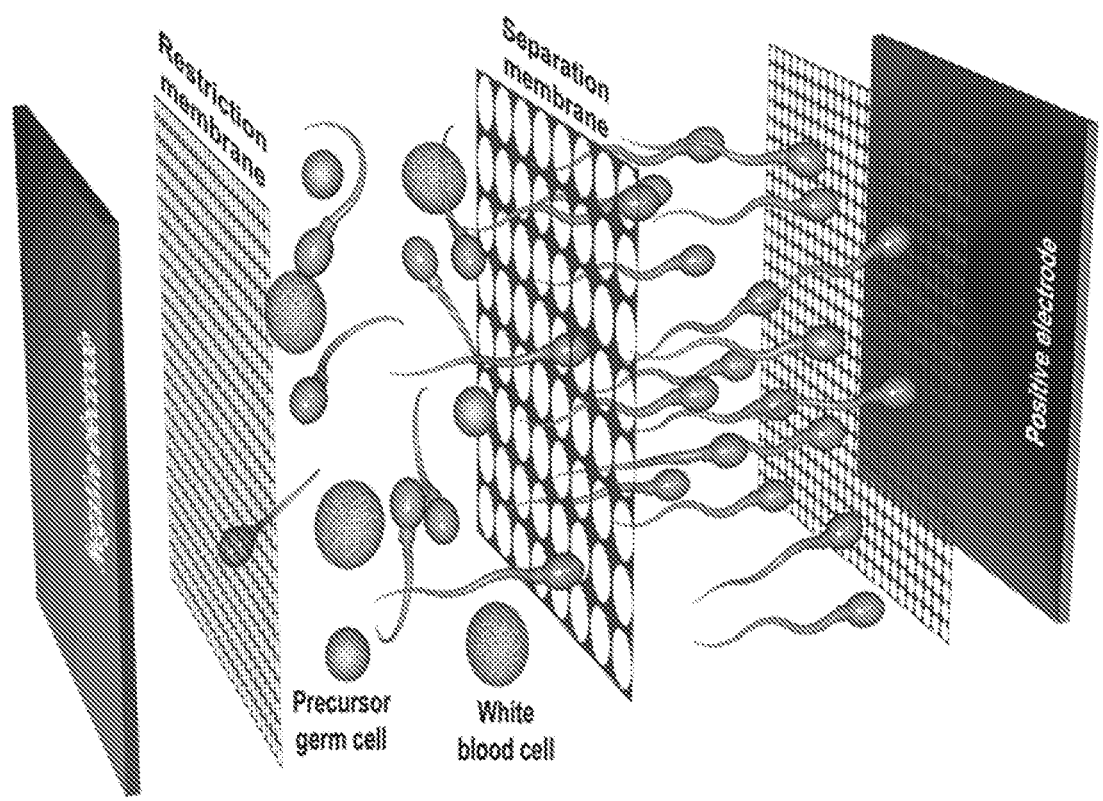
FIG. 2: Operating principle of electrophoretic sperm separation. Viable sperm migrate towards the positive cathode and pass through a separation membrane.

Although the invention has been described with reference to certain embodiments detailed herein, other embodiments can achieve the same or similar results. Variations and modifications of the invention will be obvious to those skilled in the art and the invention is intended to cover all such modifications and equivalents.

The present invention relates to the use of PVA membranes in the electrophoretic separation of sperm.

The use of PVA has several advantages for use in the separation of sperm: PVA is hydrophilic which may reduce membrane fouling by non-specific protein adsorption; it is biocompatible and neutral, aiding fabrication of membranes with low electroendosmosis (flow of bulk fluids through a membrane caused by an applied potential across membrane).

A membrane-based electrophoresis apparatus typically includes a cartridge which houses a number of membranes forming at least two chambers, cathode and anode in respective electrode chambers connected to a suitable power supply, reservoirs for samples, buffers and electrolytes, pumps for passing samples, buffers and electrolytes, and cooling means to maintain samples, buffers and electrolytes at a required temperature during electrophoresis. The cartridge contains at least three substantially planar membranes disposed and spaced relative to each other to form two chambers through which sample or solvent can be passed. A separation membrane is disposed between two restriction membranes. When the cartridge is installed in the apparatus, the restriction membranes are located adjacent to an electrode. An example of a cartridge is described in AU 738361, Descriptions of membrane-based electrophoresis can be found in U.S. Pat. Nos. 5,039,386 and 5,650,055. An apparatus particularly suitable for use in isoelectric separation applications can be found in WO 02/24314.

One electrophoresis apparatus suitable for use in the present invention comprises:
(a) a first electrolyte chamber;
(b) a second electrolyte chamber,
(c) a first sample chamber disposed between the first electrolyte chamber and the second electrolyte chamber;
(d) a second sample chamber disposed adjacent to the first sample chamber disposed and between the first electrolyte chamber and the second electrolyte chamber;
(e) a separation membrane disposed between the first sample chamber and the second sample chamber, the separation membrane preventing substantial convective mixing of contents of the first and second sample chambers;
(f) a first restriction membrane disposed between the first electrolyte chamber and the first sample chamber, the first restriction membrane preventing substantial convective mixing of contents of the first electrolyte chamber and the first sample chamber;
(g) a second restriction membrane disposed between the second sample chamber and the second electrolyte chamber, the second restriction membrane preventing substantial convective mixing of contents of the second electrolyte chamber and the second sample chamber; and
(h) electrodes disposed in the first and second electrolyte chambers.

The electrophoresis apparatus may further comprise one or more of:
(i) an electrolyte reservoir;
(j) a first sample reservoir and a second sample reservoir;
(k) means for supplying electrolyte from the electrolyte reservoir to the first and second electrolyte chambers; and
(l) means for supplying sample or liquid from at least the first sample reservoir to the first sample chamber, or from the second sample reservoir to the second sample chamber.

The apparatus may further comprise:
(m) a first electrolyte reservoir and a second electrolyte reservoir; and
(n) means for supplying electrolyte from the first electrolyte reservoir to the first electrolyte chamber and electrolyte from second electrolyte reservoir to the second electrolyte chamber.

The apparatus may further comprise one or more of:
means for circulating electrolyte from the electrolyte reservoir(s) through the electrolyte chambers forming electrolyte streams in the electrolyte chambers; and
means for circulating contents from each of the first and second sample reservoirs through the respective first and second sample chambers forming first and second sample streams in the respective sample chambers;
means for removing and replacing sample in the first or second sample reservoirs; and
means to maintain temperature of electrolyte and sample solutions.

Preparation and characterisation of PVA restriction and separation membranes is described in detail in U.S. Provisional Application No. 62/326,331 filed on 22 Apr. 2016, the content of which is herein incorporated by reference in its entirety. In brief, PVA restriction membranes were prepared by casting and annealing with the predominant stabilising mechanism in the restriction membranes being non-covalent cross-linking due to the formation of crystalline domains, and PVA separation membranes were prepared by a combination of casting and non-solvent induced phase inversion to generate a porous structure, followed by post annealing.

The present invention is further described by the following non-limiting examples.

EXAMPLES

Example 1—PVA Restriction Membrane Preparation

To prepare a PVA stock solution, a known quantity of high-purity water was added to a round bottom flask. The flask was placed in a thermostated oil bath (90° C.) and stirred under reflux. A known mass of PVA was added portions, until the desired concentration (% w/w) was achieved. The slurry was stirred at 90° C. until no undissolved gels were observed, forming a viscous solution. Following, the solution was stirred an additional 30 min at reflux to ensure complete dissolution of PVA. The solution was cooled slowly to room temperature with gentle mixing, then weighed. If necessary, high-purity water was then added to return the net mass to the starting mass to produce the desired concentration (% w/w). Following, the solution was gently stirred at room temperature for 30 minutes, and then stood overnight without stirring to remove entrained bubbles.

Stock solutions of poly(ethylene glycol) (PEG) or poly (N-vinylpyrrolidone) (PVPON) in water were prepared by dissolving appropriate PEG and PVPON in water to the desired concentration (% w/w).

PVA restriction membranes were prepared by casting and annealing method. The membrane casting solutions were prepared by mixing an appropriate mass of PVA solution, additive solution (PEG or PVPON, varied MW) and high-purity $H_2O$. The solutions were stirred for a minimum of 30 minutes to ensure all components were well mixed, then stood for 30 minutes at room temperature to allow any entrained bubbles to be collected. The membranes were cast into a membrane casting tank comprising two layers of PET substrates. Following air-drying, the membranes were annealed at 110° C. for 1 hr, then swollen for 48 hours in high-purity $H_2O$ before analysis. The membrane formulations detail is listed in Table 1.

TABLE 1

Formulations of PVA restriction membranes

| Batch No | PVA (% w/w) | PEG (% w/w) | Annealing at 110° C. |
|---|---|---|---|
| PVA-1 | $PVA_{89k}$ (10%) | 0% | Yes |
| PVA-4 | $PVA_{22k}$ (15%) | 0% | Yes |
| PVA-18 | $PVA_{22k}$ (14%) | $PEG_{8k}$ (1%) | Yes |

Example 2—PVA Separation Membrane Preparation

PVA, PEG and PVPON stock solutions were prepared as described for restriction PVA membranes.

PVA separation membranes were prepared by non-solvent induced phase inversion. In the first instance, the membranes with varying pore sizes were prepared without any support substrates for ease of characterisation. The membrane casting solutions were prepared by mixing an appropriate mass of PVA solution (89 kg/mol), additive solution (PEG or PVPON, varied MW) and high-purity $H_2O$. The solutions were stirred for a minimum of 30 minutes to ensure all components were well mixed, then stood for 30 minutes at room temperature to allow any entrained bubbles to be collected. The membranes were cast into machined wells formed in stainless steel discs (internal diameter=55 mm, well depth=1 mm), air-dried for 5 minutes, and then immersed in a non-solvent coagulation bath (200 mL).

The composition of the non-solvent bath was varied by altering the volume ratios of $H_2O$, methanol (MeOH) and ethanol (EtOH). The membranes were held in the coagulation bath for a minimum for 60 minutes. To reduce membrane shrinkage and pore collapse upon drying, after coagulation, the membranes were immersed in an acetone bath (100 mL) for 15 minutes, then removed and placed on a glass plates and air-dried. Following air-drying, the membranes were annealed at 110° C. for 1 hr, then swollen for 48 hours in 2×100 mL portions of high-purity $H_2O$ before analysis. The PVA separation membrane formulations with PEG additives are shown in Table 2. Strength of hydrated membranes fabricated from high molecular weight PVA (89-98 kg/mol) is very good; can be manipulated easily with tweezers, can be stretched.

TABLE 2

Formulation table for PVA-64, PVA-66 and PVA-67 separation membranes.

| Batch No | PVA (% w/w) | Additive (% w/w) | Phase Inversion | Annealing at 110° C. |
|---|---|---|---|---|
| PVA-64 | $PVA_{89k}$ (11.0%) | $PEG_{2k}$ (0.91%) | 64:21:15 v/v EtOH/MeOH/$H_2O$, 90 min | Yes |
| PVA-66 | $PVA_{89k}$ (11.0%) | $PEG_{2k}$ (0.91%) | 21:64:15 v/v EtOH/MeOH/$H_2O$, 90 min | Yes |
| PVA-67 | $PVA_{89k}$ (11.0%) | $PEG_{2k}$ (0.91%) | 85:15 v/v MeOH/$H_2O$, 90 min | Yes |

PVA separation membrane formulations with PVPON additive are shown in Table 3.

TABLE 3

Formulation table for PVA-80, PVA-81 PVA-83 separation membranes

| Batch No | PVA (% w/w) | Additive (% w/w) | Phase Inversion | Annealing at 110° C. |
|---|---|---|---|---|
| PVA-80 | $PVA_{89k}$ (11.8%) | $PVPON_{10k}$ (0.91%) | 85:15 v/v MeOH/$H_2O$, 90 min | Yes |
| PVA-81 | $PVA_{89k}$ (11.8%) | $PVPON_{10k}$ (0.91%) | 6.5:78.5:15 v/v EtOH/MeOH/$H_2O$, 90 min | Yes |
| PVA-83 | $PVA_{89k}$ (11.8%) | $PVPON_{10k}$ (0.91%) | 19.5/65.5:15 v/v MeOH/$H_2O$, 90 min | Yes |

Example 3—Use of PVA Membranes in the Separation of Sperm

Figure 3:
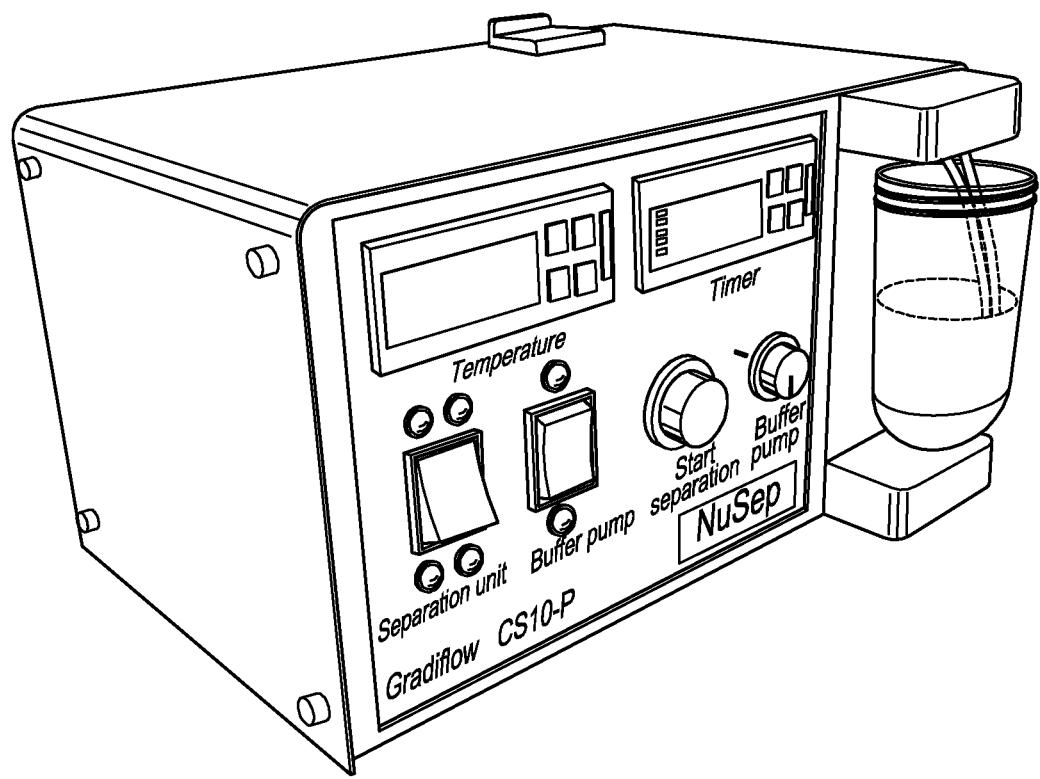
FIG. 3: CS10 electrophoresis separation apparatus.

The NuSep CS10 electrophoresis apparatus was used to carry out tests to compare PAm and PVA restriction membranes. A schematic diagram of the CS10 apparatus is shown in FIG. 3. The CS10 apparatus enables the precise control of run time, voltage and circulating buffer rates and is suitable for the processing of a diverse range of samples.

Restriction and separation membranes were cut into the required size using an appropriate die and assembled in a cartridge, wherein the cartridge comprises a separation membrane sandwiched between two restriction membranes. The cartridge was inserted into the CS10 apparatus for electrophoresis.

Electrophoresis of Bovine Sperm

Electrophoresis of bovine sperm samples was performed in the CS10 apparatus with a 8 μm polycarbonate separation membrane and either (a) PAm restriction membranes or (b) PVA restriction membranes. Samples were processed at 35 volts, a maximum current of 50 mA and 5 minutes running time. Original, harvested and retained/residual samples were stained with Eosine-Nigrosine (EN) to assess sperm viability and stained with Aniline Blue (AB) to assess DNA fragmentation. Motility was assessed by eye under 100× light microscope.

The results for PAm restriction membranes are presented in Table 4.

TABLE 4

Results for bovine sperm separation with PAm restriction membranes

| | Sperm count (×10⁶ cells/ml) | | | Harvest rate (%) | | EN stain Live (%) | | | AB stain Negative (%) | | | Motility (%) | | |
|---|---|---|---|---|---|---|---|---|---|---|---|---|---|---|
| | O | H | R | H | R | O | H | R | O | H | R | O | H | R |
| E1 | 56 | 9.3 | 43.3 | 19 | 78 | 77 | 89 | 65 | 97 | 98 | 94 | 64 | 85 | 62 |
| E2 | 43 | 7.5 | 36.5 | 17.3 | 84.9 | 37 | 59 | 28 | 99 | 100 | 100 | 26 | 52 | 12 |
| E3 | 12 | 2.4 | 10.5 | 20 | 87.5 | 67 | 81 | 54 | 100 | 100 | 100 | 58 | 75 | 36 |

(O = original, H = harvested and R = retained/residual)

The results for PVA restriction membranes are presented in Table 5.

TABLE 5

Results for bovine sperm separation with PVA restriction membranes

| | Sperm count (×10⁶ cells/ml) | | | Harvest rate (%) | | EN stain Live (%) | | | AB stain Negative (%) | | | Motility (%) | | |
|---|---|---|---|---|---|---|---|---|---|---|---|---|---|---|
| | O | H | R | H | R | O | H | R | O | H | R | O | H | R |
| E1 | 22 | 6.6 | 13.5 | 30.2 | 61.4 | 72 | 86 | 74 | 100 | 100 | 100 | 71 | 90 | 63 |
| E2 | 28 | 6.8 | 16.7 | 24.2 | 59.6 | 68 | 83 | 71 | 100 | 100 | 100 | 73 | 86 | 56 |
| E3 | 31 | 6.7 | 21.6 | 21.5 | 69.7 | 71 | 80 | 66 | 100 | 100 | 100 | 69 | 87 | 50 |

(O = original, H = harvested and R = retained)

Electrophoresis of Human Sperm

Electrophoresis of human sperm samples was performed in the CS10 apparatus with a 8 μm polycarbonate separation membrane and either (a) PAm restriction membranes or (b) PVA restriction membranes. Samples were processed and analysed as described above.

The results for PAm restriction membranes are presented in Table 6.

TABLE 6

Results for bovine sperm separation with PAm restriction membranes

| | Sperm count (×10⁶ cells/ml) | | | Harvest rate (%) | | EN stain Live (%) | | | AB stain Negative (%) | | | Motility (%) | | |
|---|---|---|---|---|---|---|---|---|---|---|---|---|---|---|
| | O | H | R | H | R | O | H | R | O | H | R | O | H | R |
| E1 | 23 | 4.5 | 18.4 | 19.6 | 79.4 | 61 | 83 | 35 | 82 | 95 | 63 | 64 | 86 | 43 |
| E2 | 19 | 3.9 | 15.4 | 20 | 80 | 72 | 96 | 23 | 84 | 95 | 66 | 67 | 92 | 34 |
| E3 | 52 | 9.5 | 23.5 | 18 | 46 | 61 | 78 | 43 | 64 | 90 | 32 | 45 | 73 | 32 |

(O = original, H = harvested and R = retained/residual)

The results for PVA restriction membranes are presented in Table 7.

TABLE 7

Results for bovine sperm separation with PAm restriction membranes

| | Sperm count (×10⁶ cells/ml) | | | Harvest rate (%) | | EN stain Live (%) | | | AB stain Negative (%) | | | Motility (%) | | |
|---|---|---|---|---|---|---|---|---|---|---|---|---|---|---|
| | O | H | R | H | R | O | H | R | O | H | R | O | H | R |
| E1 | 21 | 3.9 | 16.2 | 19.5 | 77.5 | 59 | 81 | 33 | 61 | 85 | 50 | 62 | 85 | 35 |
| E2 | 20 | 3.6 | 15.8 | 18 | 79 | 63 | 84 | 40 | 55 | 75 | 35 | 55 | 74 | 33 |

(O = original, H = harvested and R = retained/residual)

Comparison of PAm and PVA Membranes

A comparison of PAm and PVA restriction membranes in the separation of bovine and human sperm is presented in Table 8.

TABLE 8

Comparison of PAm and PVA restriction membranes in the separation of bovine and human sperm

|  | Harvest rate (%) | EN stain Live (%) | Motility (%) |
|---|---|---|---|
| Bovine PAm | 18.8 | 16 | 21 |
| Bovine PVA | 25.3 | 12 | 16 |
| Human PAm | 19.2 | 21 | 25 |
| Human PVA | 18.75 | 22 | 21 |

No statistically significant differences were observed between PVA and Pam restriction membranes for the separation of bovine or human sperm. Accordingly, PVA restriction membranes may be substituted for PAm restriction membranes for sperm separation.

What is claimed is:

1. A method of using at least one physically cross-linked biocompatible polymeric membrane in the separation of sperm by electrophoresis, wherein the membrane comprises poly (vinyl alcohol) (PVA).

2. The method of claim 1, wherein the membrane comprising PVA does not contain polyacrylamide (PAm).

3. The method of claim 1, wherein the membrane comprising PVA is a restriction membrane that allows passage of an electrical field but does not allow passage of sperm.

4. The method of claim 3, wherein the restriction membrane has a molecular weight cut off (MWCO) of less than 15 kDa.

5. The method of claim 4, wherein the restriction membrane is prepared by a casting and annealing method.

6. The method of claim 1, wherein the membrane comprising PVA is a porous size exclusion membrane (separation membrane).

7. The method of claim 6, wherein the separation membrane has a pore size of less than 10 μm.

8. The method of claim 6, wherein the separation membrane is prepared by non-solvent induced phase inversion method followed by post annealing.

9. A method for separating sperm from a first solution into a second solution, the method comprising the steps of:
providing the first solution to a membrane stack comprising a separation membrane disposed between first and second physically cross-linked biocompatible polymeric restriction membranes comprising PVA, wherein the first solution lies between the first restriction membrane and the separation membrane and wherein the separation membrane has a preselected pore size; and
applying an electrical field across the stack,
wherein sperm in the first solution that have a negative charge and are smaller than the preselected pore size move towards the anode and pass through the separation membrane into the second solution which lies between the separation membrane and the second restriction membrane.

10. The method of claim 9, wherein the restriction and separation membranes do not contain PAm.

11. The method of claim 9, wherein the separation membrane is a physically cross-linked biocompatible polymeric separation membrane comprising PVA.

12. A method for separating sperm from a first solution into a second solution, the method comprising the steps of:
separating the first and second solutions by means of a physically cross-linked biocompatible polymeric separation membrane comprising PVA, wherein the separation membrane has a preselected pore size; and
applying an electric field across the first and second solutions, wherein sperm in the first solution that have a negative charge and are smaller than the preselected pore size move towards the anode and pass through the separation membrane into the second solution.

13. The method of claim 12, wherein the separation membrane does not contain PAm.

* * * * *